United States Patent
Itonaga et al.

(10) Patent No.: US 10,962,531 B2
(45) Date of Patent: Mar. 30, 2021

(54) METHOD OF CAPTURING EXOSOMES

(71) Applicant: JVC KENWOOD CORPORATION, Yokohama (JP)

(72) Inventors: Makoto Itonaga, Yokohama (JP); Yuichi Hasegawa, Yokohama (JP); Koji Tsujita, Yokohama (JP); Masayuki Ono, Yokohama (JP); Shigehiko Iwama, Yokohama (JP); Makoto Igarashi, Yokohama (JP)

(73) Assignee: JVC KENWOOD CORPORATION, Yokohama (JP)

(*) Notice: Subject to any disclaimer, the term of this patent is extended or adjusted under 35 U.S.C. 154(b) by 635 days.

(21) Appl. No.: 15/897,418

(22) Filed: Feb. 15, 2018

(65) Prior Publication Data

US 2018/0180604 A1 Jun. 28, 2018

Related U.S. Application Data

(63) Continuation of application No. PCT/JP2016/068271, filed on Jun. 20, 2016.

(30) Foreign Application Priority Data

Aug. 21, 2015 (JP) .............................. JP2015-163336

(51) Int. Cl.
*G01N 33/543* (2006.01)
*G01N 33/536* (2006.01)
*G01N 33/537* (2006.01)

(52) U.S. Cl.
CPC ......... *G01N 33/543* (2013.01); *G01N 33/536* (2013.01); *G01N 33/537* (2013.01);
(Continued)

(58) Field of Classification Search
USPC .......... 435/7.1, 7.2, 7.21, 7.23; 436/64, 523, 436/524, 525, 526, 538, 541
See application file for complete search history.

(56) References Cited

U.S. PATENT DOCUMENTS

| | | |
|---|---|---|
| 2013/0203061 A1 | 8/2013 | Kuslich et al. |
| 2014/0377779 A1 | 12/2014 | Yong et al. |
| 2016/0033486 A1* | 2/2016 | Itonaga ................ G01N 33/487 435/287.2 |

FOREIGN PATENT DOCUMENTS

| | | |
|---|---|---|
| JP | 2012-508577 A | 4/2012 |
| WO | 2009/092386 A2 | 7/2009 |
| WO | 2014/0168020 A1 | 10/2014 |

OTHER PUBLICATIONS

European extended search report dated Jul. 5, 2018 for corresponding application No. 16838894.0.
(Continued)

*Primary Examiner* — Christopher L Chin
(74) *Attorney, Agent, or Firm* — Nath, Goldberg & Meyer; Jerald L. Meyer

(57) ABSTRACT

A first sample solution including exosomes including first to third detection target substances is mixed with a first buffer solution including first nanoparticles including first binding substances which bind to the first detection target substances. The first detection target substances and the first binding substances are bound together, so as to form first complexes of the exosomes and the first nanoparticles. The first complexes are isolated from a mixed solution of the first sample solution and the first buffer solution. The second detection target substances and the second binding substances are bound together, so as to capture the first complexes on a substrate. The second binding substances are fixed onto the substrate. A second buffer solution including second nanoparticles including third binding substances
(Continued)

which bind to the third detection target substances is reacted with the first complexes.

4 Claims, 15 Drawing Sheets

(52) U.S. Cl.
CPC . *G01N 33/54306* (2013.01); *G01N 33/54313* (2013.01); *G01N 33/54346* (2013.01); *G01N 33/54326* (2013.01)

(56) References Cited

OTHER PUBLICATIONS

Gholamreza, Tavoosidana, et al.; "Multiple recognition assay reveals prostasomes as promising plasma biomarkers for prostate cancer"; PNAS, vol. 8 No. 21; May 24, 2011 pp. 8809-8814.

Clayton, et al., "Analysis of antigen presenting cell derived exosomes, based on immuno-magnetic isolation and flow cytometry", Journal of Immunological Method, vol. 247, pp. 163-174, 2001.

PCT/ISA/237 dated Aug. 30, 2016 issued in corresponding International Application No. PCT/JP2016/068271.

\* cited by examiner

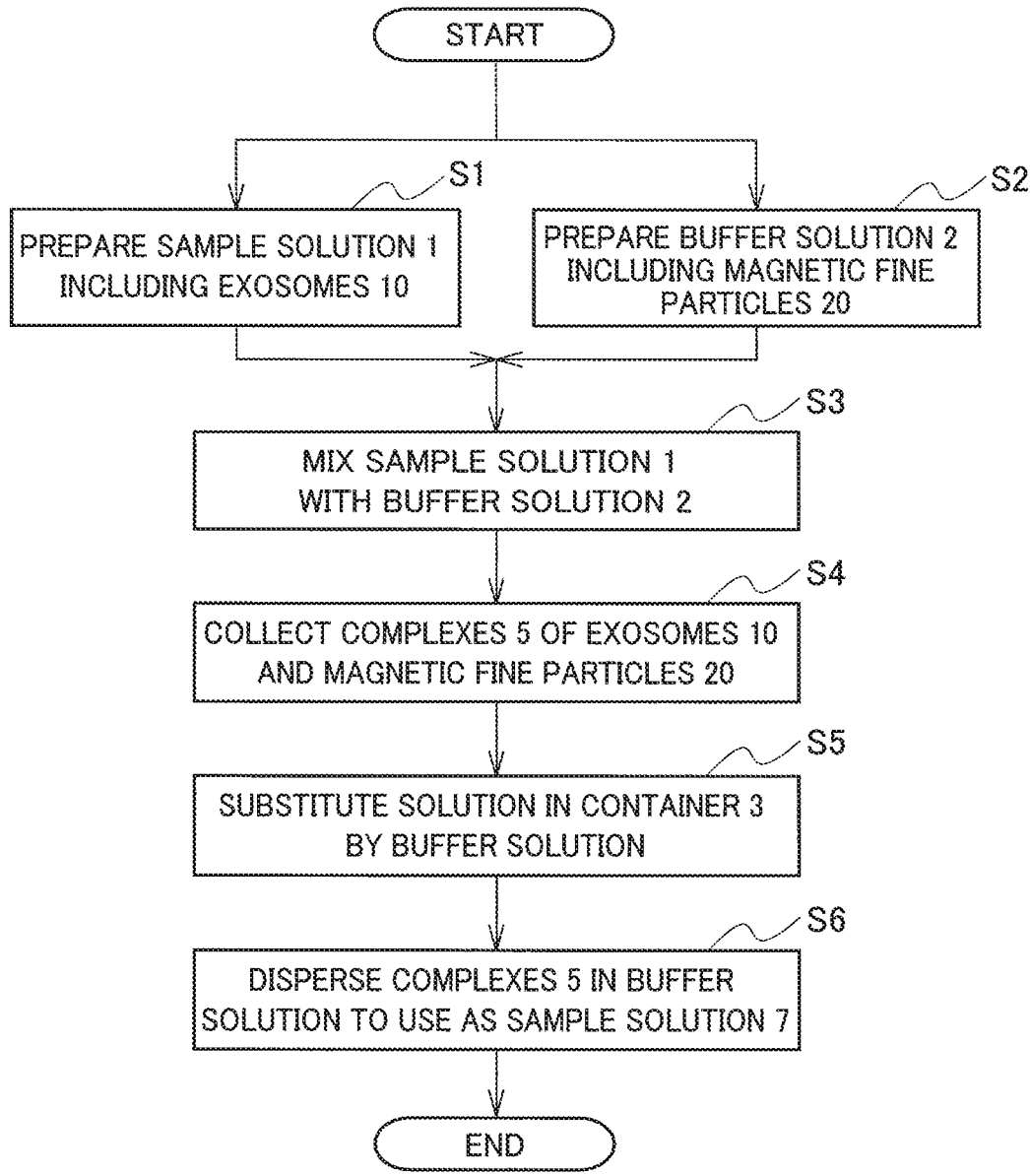

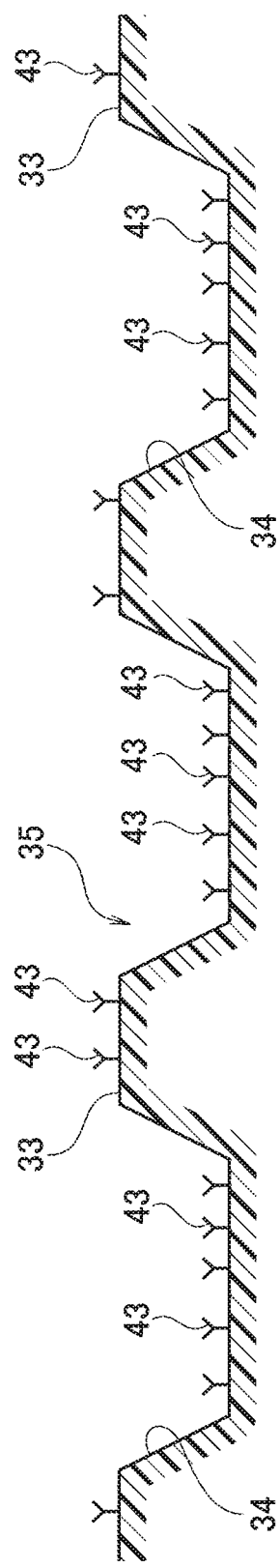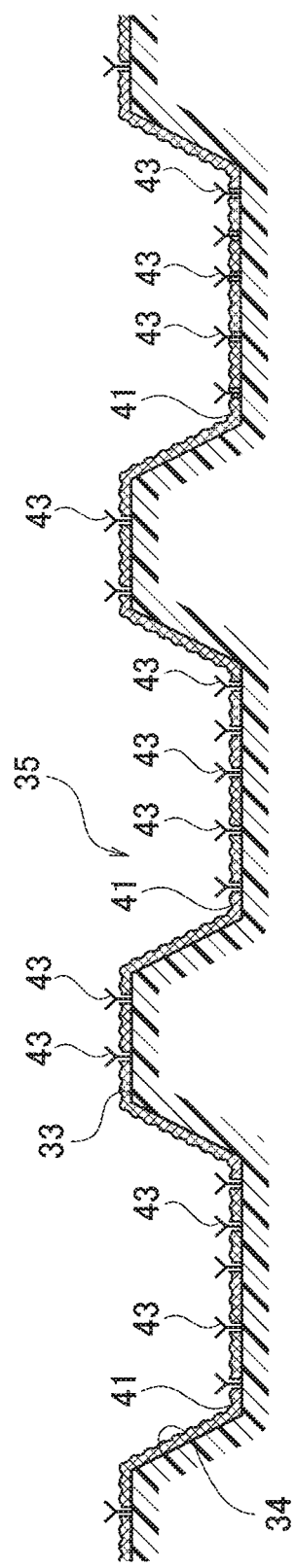

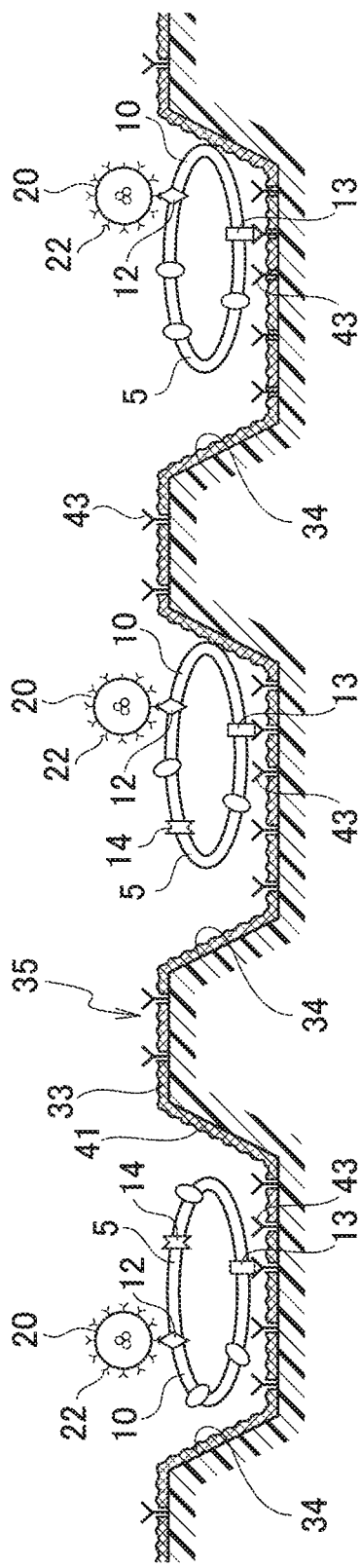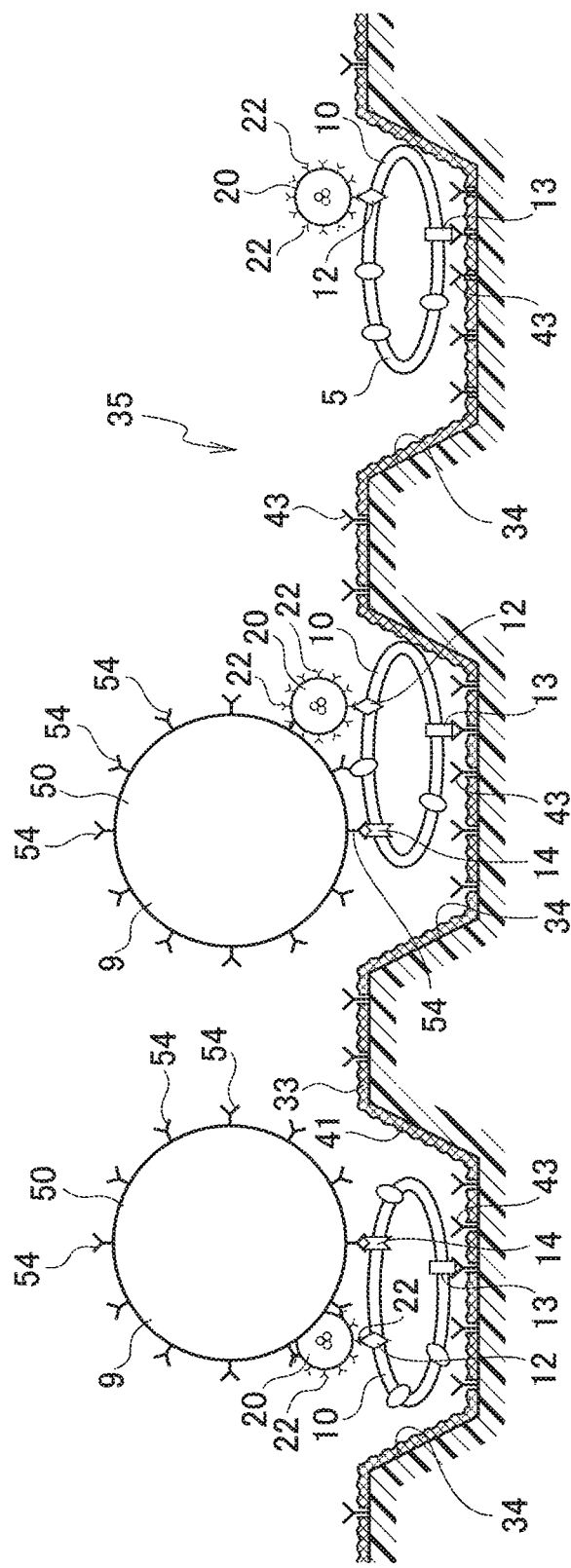

METHOD OF CAPTURING EXOSOMES

CROSS REFERENCE TO RELATED APPLICATION

This application is a Continuation of PCT Application No. PCT/JP2016/068271, filed on Jun. 20, 2016, and claims the priority of Japanese Patent Application No. 2015-163336, filed on Aug. 21, 2015, the entire contents of both of which are incorporated herein by reference.

BACKGROUND

The present disclosure relates to a method of capturing exosomes secreted by various kinds of cells.

Analysis is widely used that quantitatively analyzes disease detection and therapeutic effects by detecting particular antigens (or antibodies) as biomarkers associated with diseases. In recent years, membrane vesicles referred to as exosomes have been expected to serve as new biomarkers.

Exosomes are contained in blood, lymph, saliva, urine, breast milk, semen, and the like. Exosomes dispersed in liquid are substantially spherical and typically have a diameter of about 100 nm. Exosomes are covered with lipid bilayers. Lipid bilayers keep various kinds of substances thereon such as proteins. Lipid bilayers enclose various proteins and nucleic acids such as miRNA. Exosomes have several names and are also referred to as microvesicles and extracellular vesicles.

International Publication WO 2009/092386 (Patent Literature 1) discloses a method of capturing and analyzing exosomes by immunoassays of an enzyme-linked immunosorbent assay (ELISA).

SUMMARY

Exosomes typically contains various kinds of proteins. Among those, proteins to be identified are present on surfaces of lipid bilayers, and examples thereof include a transmembrane protein, an adhesion molecule, a membrane transport protein, a membrane fusion protein, and a glycoprotein. Hereinafter, these proteins are collectively referred to as "proteins". Exosomes can be selectively detected if several kinds of proteins could be identified per exosome. Such a selective detection can enhance specificity of diseases to be detected, and an improvement in precision or accuracy of diagnoses is thus expected.

The conventional method of capturing exosomes as disclosed in Patent Literature 1 can recognize two kinds of proteins per exosome, but has not achieved simultaneous identification of three kinds of proteins per exosome.

The conventional method thus needs to capture and analyze exosomes several times by use of different antibodies, which complicates the process. It is still difficult to recognize whether three kinds of proteins are present simultaneously on one exosome through the process of capturing and analyzing the exosomes several times.

An aspect of one or more embodiments provides a method of capturing exosomes including the steps of: mixing a first sample solution including exosomes expressing first detection target substances, second detection target substances, and third detection target substances with a first buffer solution including first nanoparticles fixing first binding substances which bind to the first detection target substances, so as to bind the first detection target substances and the first binding substances together to form first complexes of the exosomes and the first nanoparticles; isolating the first complexes from a mixed solution of the first sample solution and the first buffer solution; binding the second detection target substances of the first complexes and second binding substances which bind to the second detection target substances together, so as to capture the first complexes on a substrate, the second binding substances being fixed onto the substrate; and reacting a second buffer solution including second nanoparticles fixing third binding substances which bind to the third detection target substances with the first complexes captured on the substrate, and binding the third detection target substances and the third binding substances together, so as to bind the second nanoparticles to the exosomes of the first complexes which are captured on the substrate.

BRIEF DESCRIPTION OF THE DRAWINGS

FIG. 1 is a flow chart for describing a method of forming complexes of exosomes and first nanoparticles.

FIG. 12A is a schematic cross-sectional view showing a state in which the antibodies are fixed to the track region.

FIG. 12B is a schematic cross-sectional view showing a state in which a block layer is formed on the track region.

FIG. 13A is a schematic cross-sectional view showing a state in which the complexes are fixed to grooves in the track region.

FIG. 13B is a schematic cross-sectional view showing a state in which the complexes in which the magnetic nanoparticles and the nanoparticles bind to the exosomes are fixed to grooves in the track region.

DETAILED DESCRIPTION

[Formation of Complexes of Exosomes and First Nanoparticles]

First, a method of forming complexes of exosomes and first nanoparticles is described below with reference to FIG. 1 to FIG. 6.

Figure 2A:
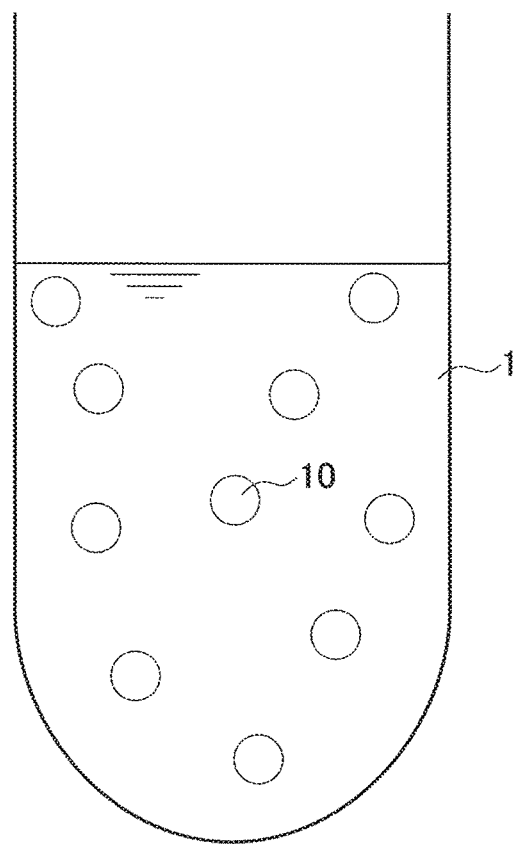
FIG. 2A is a schematic cross-sectional view of a sample solution including exosomes.
Figure 2B:
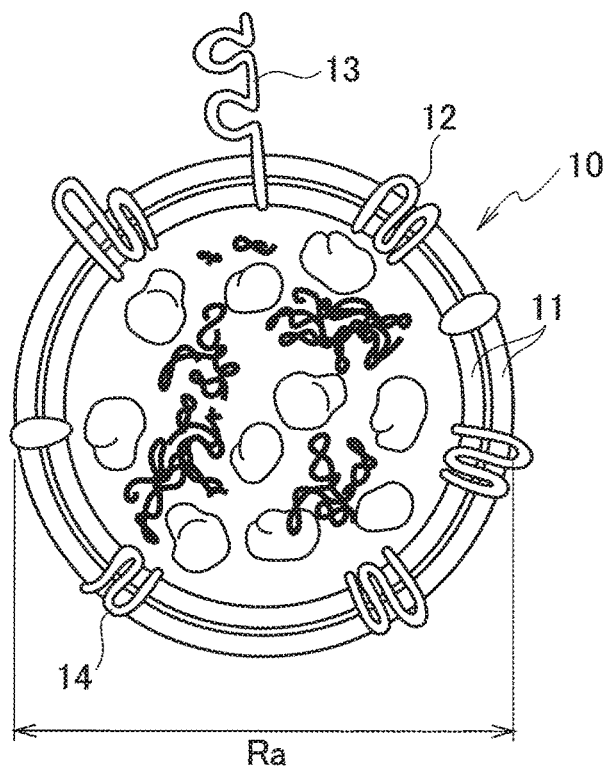
FIG. 2B is a schematic cross-sectional view of a exosome.

FIG. 1 is a flowchart for describing the method of forming complexes of exosomes 10 and magnetic nanoparticles 20. FIG. 2A is a schematic cross-sectional view of a sample solution 1 including the exosomes 10. FIG. 2B is a schematic cross-sectional view of the exosome 10. Although the exosomes 10 have various diameters, FIG. 2A and other drawings illustrate the exosomes 10 having the same diameter.

In step S1 shown in FIG. 1, an operator prepares the sample solution 1 (a first sample solution) including the exosomes 10 to be detected, as shown in FIG. 2A.

As shown in FIG. 2B, the exosome 10 is covered with lipid bilayers 11. The lipid bilayers 11 contain various kinds of proteins such as a transmembrane protein. The number and positions of proteins in the lipid bilayers 11 vary depending on the type of exosomes and depending on each individual. The exosomes are identified by an antigen-antibody reaction using these surface molecules as antigens. Various kinds of proteins, such as CD63, CD9, and Rab-5b, as surface molecules serving as antigens have been reported in many theses. In FIG. 2B, three kinds of proteins (detection target substances) serving as antigens for identifying the exosomes are indicated by reference numerals 12, 13, and 14.

An average particle diameter Ra of the exosomes 10 is 100 nm, for example.

As used herein, the average particle diameter Ra of the exosomes 10 refers to an average of particle diameters of the exosomes 10 measured by an arbitrary measurement method. Examples of measurement methods include a wet measurement method which measures the exosomes 10 included in a solution by use of nanoparticle tracking analysis, and a dry measurement method which measures the exosomes 10 kept in their forms with a transmission electron microscope.

In the latter measurement method, a specimen including the exosomes 10 is subjected to predetermined treatment according to a method used for measuring cells in order to measure the exosomes 10 kept in their forms in the dry process.

In particular, a specimen is fixed to a substrate, and repeatedly impregnated with ethanol having different concentrations, from ethanol with a low concentration to ethanol with purity of 100%, so as to gradually increase the concentration of ethanol in several steps. Accordingly, the moisture contained in the specimen is substituted by the ethanol so that the specimen is dehydrated.

Thereafter, the specimen is impregnated with a solution containing synthetic resin soluble in the ethanol, so as to substitute the ethanol by the synthetic resin. The operator laminates and measures the specimen substituted by the synthetic resin.

Alternatively, the specimen including the exosomes 10 may be quick-frozen, so that the dehydrated exosomes 10 kept in their forms are measured.

Figure 3A:
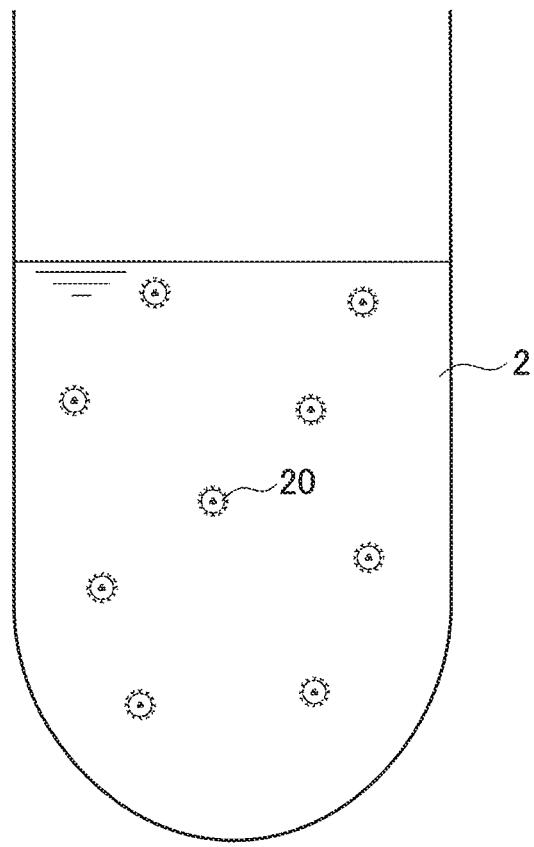
FIG. 3A is a schematic view of a buffer solution including magnetic nanoparticles.
Figure 3B:
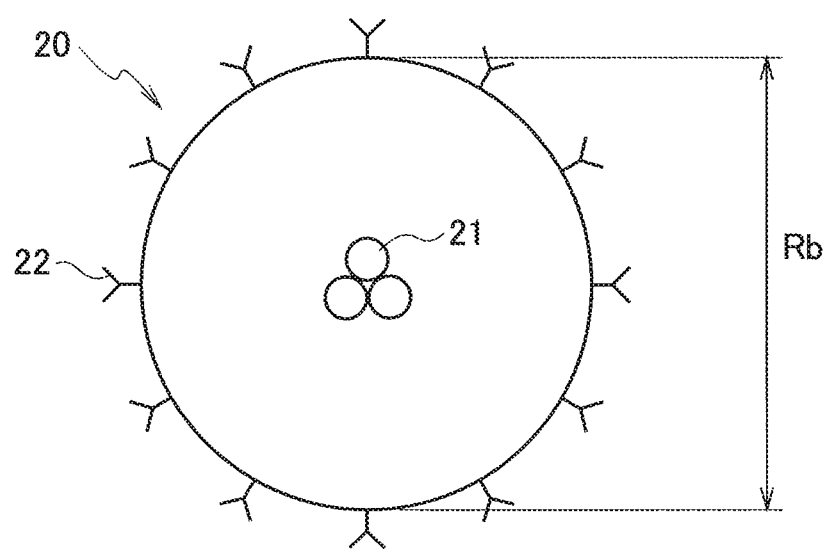
FIG. 3B is a schematic view of a magnetic fine particle.

FIG. 3A is a schematic view of a buffer solution 2 including the magnetic nanoparticles 20. FIG. 3B is a schematic view of the magnetic fine particle 20.

In step S2, the operator prepares the buffer solution 2 (a first buffer solution) including the magnetic nanoparticles 20 (first nanoparticles), as shown in FIG. 3A.

The magnetic fine particle 20 is made of synthetic resin such as polystyrene formed into a substantially spherical shape as shown in FIG. 3B. The magnetic fine particle 20 encloses magnetic substances 21 such as iron oxide. Antibodies 22 (first binding substances) which specifically bind to antigens 12 (first detection target substances) of the exosome 10 are fixed to the surface of the magnetic fine particle 20. A particle diameter Rb of the magnetic fine particle 20 will be described below.

Figure 4:
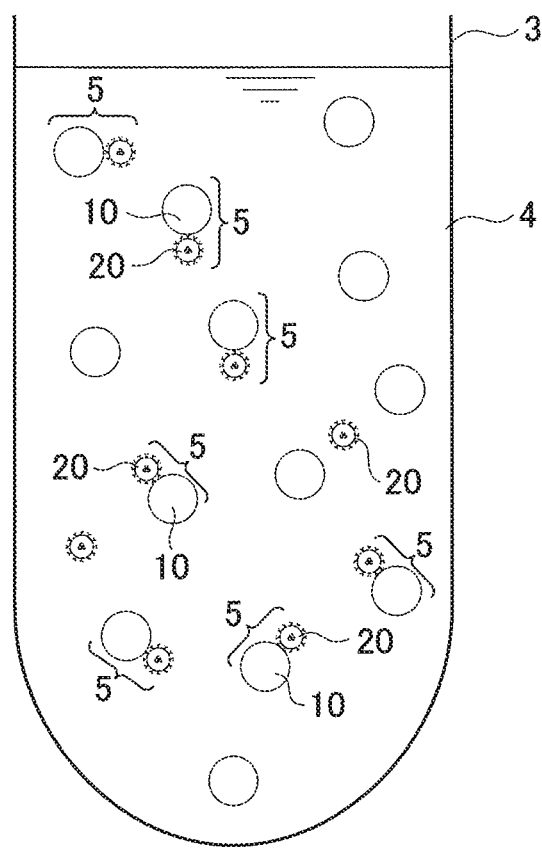
FIG. 4 is a schematic cross-sectional view of a mixed solution of the sample solution including the exosomes and the buffer solution including the magnetic nanoparticles.

FIG. 4 is a schematic cross-sectional view of a mixed solution 4 of the sample solution 1 including the exosomes 10 and the buffer solution 2 including the magnetic nanoparticles 20.

In step S3, the operator injects the sample solution 1 and the buffer solution 2 into a container 3 such as a microtube or a column and mixes together, as shown in FIG. 4. The operator incubates the mixed solution for an appropriate time so as to promote the antigen-antibody reaction.

Due to the incubation, complexes 5 (first complexes) of the exosomes 10 and the magnetic nanoparticles 20 in which the antigens 12 and the antibodies 22 are specifically bound together are formed in the mixed solution 4. Depending on the sample solution, the exosomes not including the antigens 12 may be present. The exosomes not including the antigens 12 are dispersed in the mixed solution 4 without being bound to the magnetic nanoparticles 20.

Figure 5:
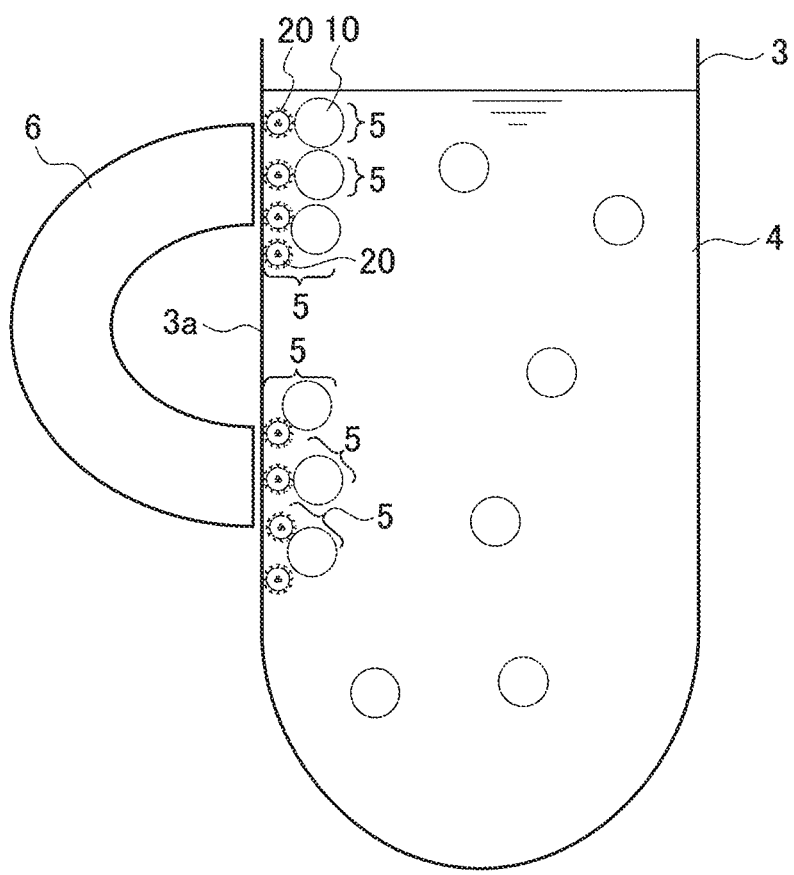
FIG. 5 is a schematic cross-sectional view showing a state in which the complexes are magnetically collected.

FIG. 5 is a schematic cross-sectional view showing a state in which the complexes 5 are magnetically collected.

In step S4, the operator magnetically collects the complexes 5 with a magnet 6 or the like, as shown in FIG. 5. For example, the magnet 6 is brought close to a side surface 3a of the container 3, so that the complexes 5 gather on the side surface 3a around the magnet 6. Accordingly, the complexes 5 can be isolated from the mixed solution 4 in step S4.

The method of isolating the complexes 5 is not limited to the magnetic collection. For example, particles carrying electric charges may be used instead of the magnetic nanoparticles 20. Since exosomes to which particles carrying electric charges are fixed differ from exosomes without particles carrying electric charges in the amount of the electric charges, the respective exosomes are sorted out from each other by use of the characteristics of different actions in an electric field. The complexes 5 may be isolated from the mixed solution 4 with a cell sorter based on flow cytometry, for example.

When the size of the magnetic nanoparticles 20 is extremely small, the degree of magnetization induced by an external magnetic field is small. A typical permanent magnet thus may not be able to magnetically gathering the complexes 5 efficiently. In such a case, magnetic collection by high gradient magnetic separation is preferably used.

In step S5, the operator substitutes the mixed solution 4 in the container 3 by a buffer solution. The substitution of the mixed solution 4 in the container 3 by the buffer solution is preferably repeated several times. The exosomes not including the antigens 12 dispersed in the mixed solution 4 are removed through the substitution by the buffer solution.

In step S6, the operator moves the magnet 6 away from the container 3 so that the complexes 5 isolated by the magnetic collection are dispersed again in the buffer solution. A preferable dispersed state can be obtained through additional dispersion treatment such that ultrasonic waves are applied to the container 3, for example.

Figure 6:
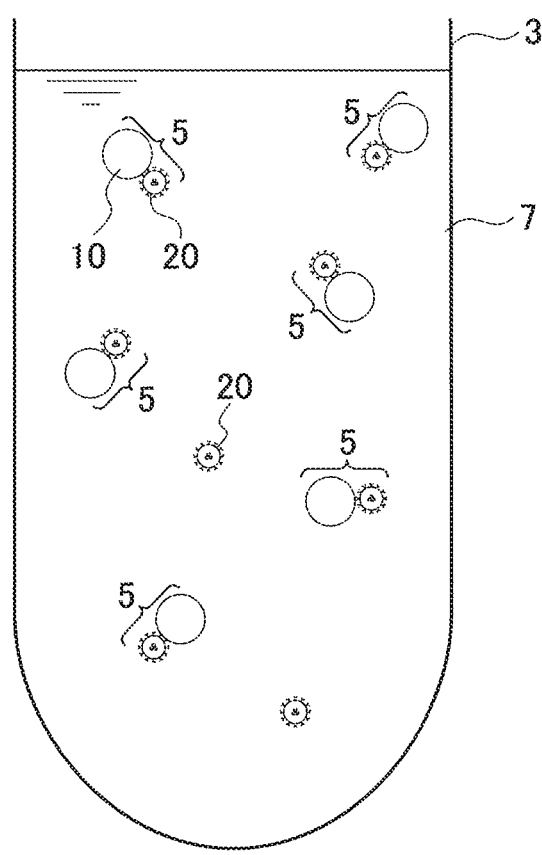
FIG. 6 is a schematic cross-sectional view of the sample solution in which the complexes are dispersed.

FIG. 6 is a schematic cross-sectional view of a sample solution 7 in which the complexes 5 are dispersed.

A suspension obtained such that the complexes 5 are dispersed again in the buffer solution through the dispersion treatment in step S6 is used as the sample solution 7 (a second sample solution), as shown in FIG. 6.

Next, a method of capturing the exosomes is described below with reference to FIG. 7A to FIG. 13B.

[Exosome Capture Unit]

First, a configuration of an exosome capture unit for capturing the exosomes is described with reference to FIG. 7A, FIG. 7B, and FIG. 8.

Figure 7A:
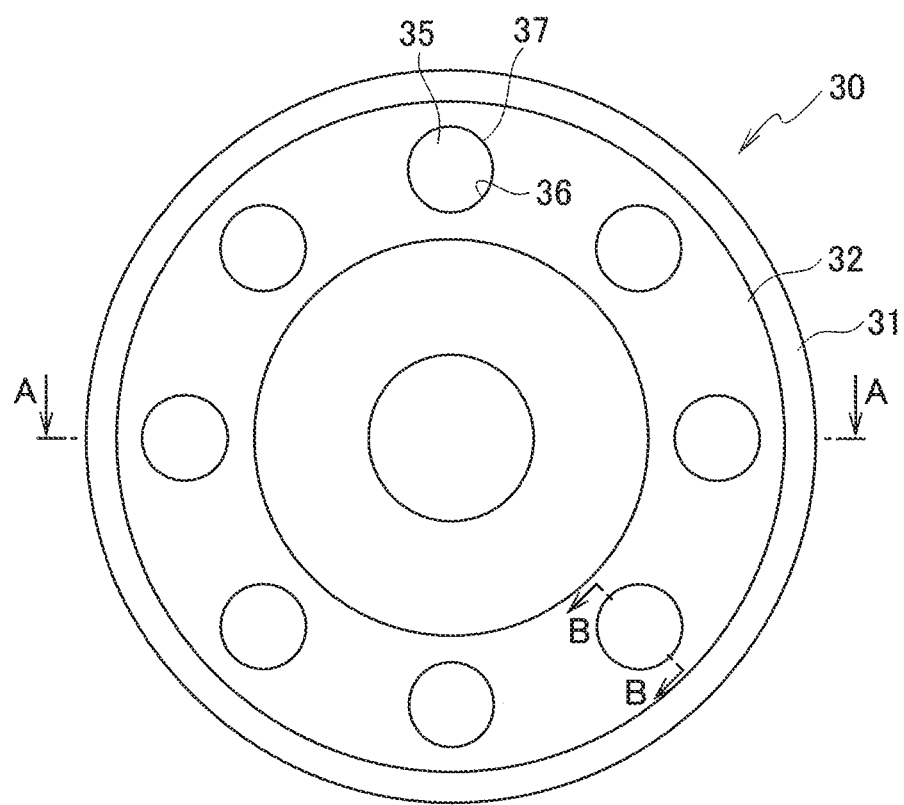
FIG. 7A is a schematic top view of the exosome capture unit.

FIG. 7A is a schematic top view of the exosome capture unit 30. FIG. 7B is a schematic cross-sectional view taken along line A-A in FIG. 7A. FIG. 7C is a schematic cross-sectional view for describing that a cartridge 32 is detachable from a substrate 31. FIG. 8 is a partly-enlarged perspective view cross-sectioned along line B-B in FIG. 7A.

As shown in FIG. 7A, the exosome capture unit 30 includes the substrate 31 and the cartridge 32.

The substrate 31 is formed into a circular shape having substantially the same dimensions as optical discs such as Blu-ray discs (BDs), digital versatile discs (DVDs), and compact discs (CDs). The substrate 31 is formed of resin material such as polycarbonate resin or cycloolefin polymer, commonly used for optical discs.

Figure 8:
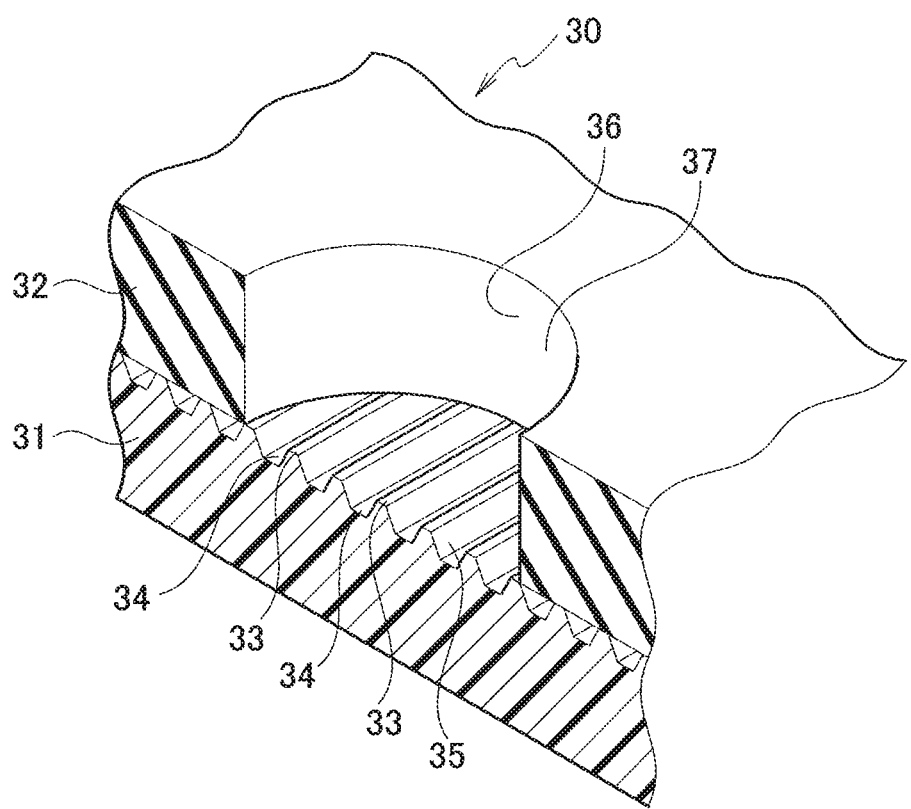
FIG. 8 is an enlarged perspective view showing a well cross-sectioned along line B-B in FIG. 7A.

As shown in FIG. 8, the surface of the substrate 31 includes a track region 35 provided with convex regions 33 and grooves 34 alternately arranged in a radial direction. The convex regions 33 and the grooves 34 are formed in a spiral from the inner side to the outer side of the substrate 31. The convex regions 33 correspond to lands of an optical disc. The grooves 34 correspond to grooves of an optical disc.

As shown in FIG. 7A, the cartridge 32 has a ring-like shape. The cartridge 32 is provided with a plurality of cylindrical penetration holes 36 arranged along the circumferential direction.

Figure 7B:
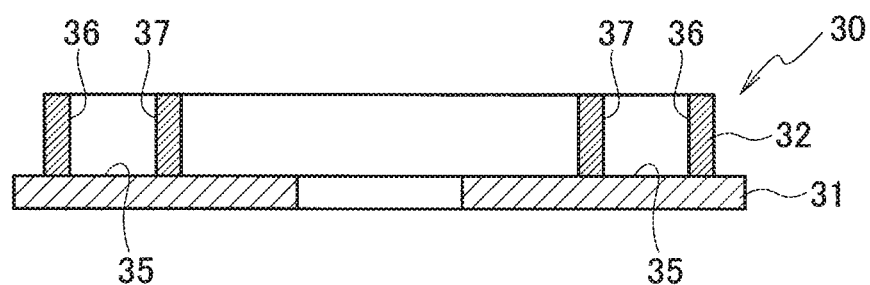
FIG. 7B is a schematic cross-sectional view taken along line A-A in FIG. 7A.
Figure 7C:
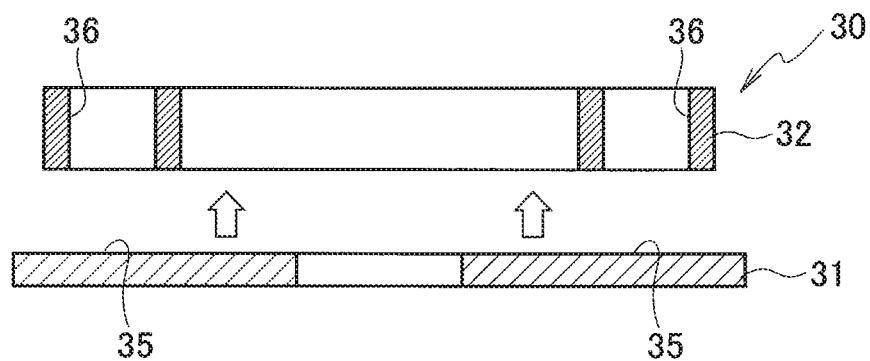
FIG. 7C is a schematic cross-sectional view for describing that a cartridge 32 is detachable from a substrate.

As shown in FIG. 7B and FIG. 8, the exosome capture unit 30 includes a plurality of wells 37 defined by the penetration holes 36 of the cartridge 32 and the track region 35 of the substrate 31. The inner surface of the penetration holes 36 corresponds to the inner surface of the wells 37, and the track region 35 of the substrate 31 corresponds to the bottom of the wells 37. The wells 37 each serve as a holder for storing the sample solution 7 and the like. A gasket made of an elastically-deformed material such as silicone rubber is preferably placed between the penetration holes 36 and the substrate 31 so as to reduce the risk of leakage of the solution.

As shown in FIG. 7C, the cartridge 32 is detachable from the substrate 31. The captured exosomes are detected only by use of the substrate 31 detached from the cartridge 32.

[Capture of Exosomes]

Next, a method of capturing the exosomes 10 by the exosome capture unit 30 is described below with reference to FIG. 9 to FIG. 15.

Figure 9:
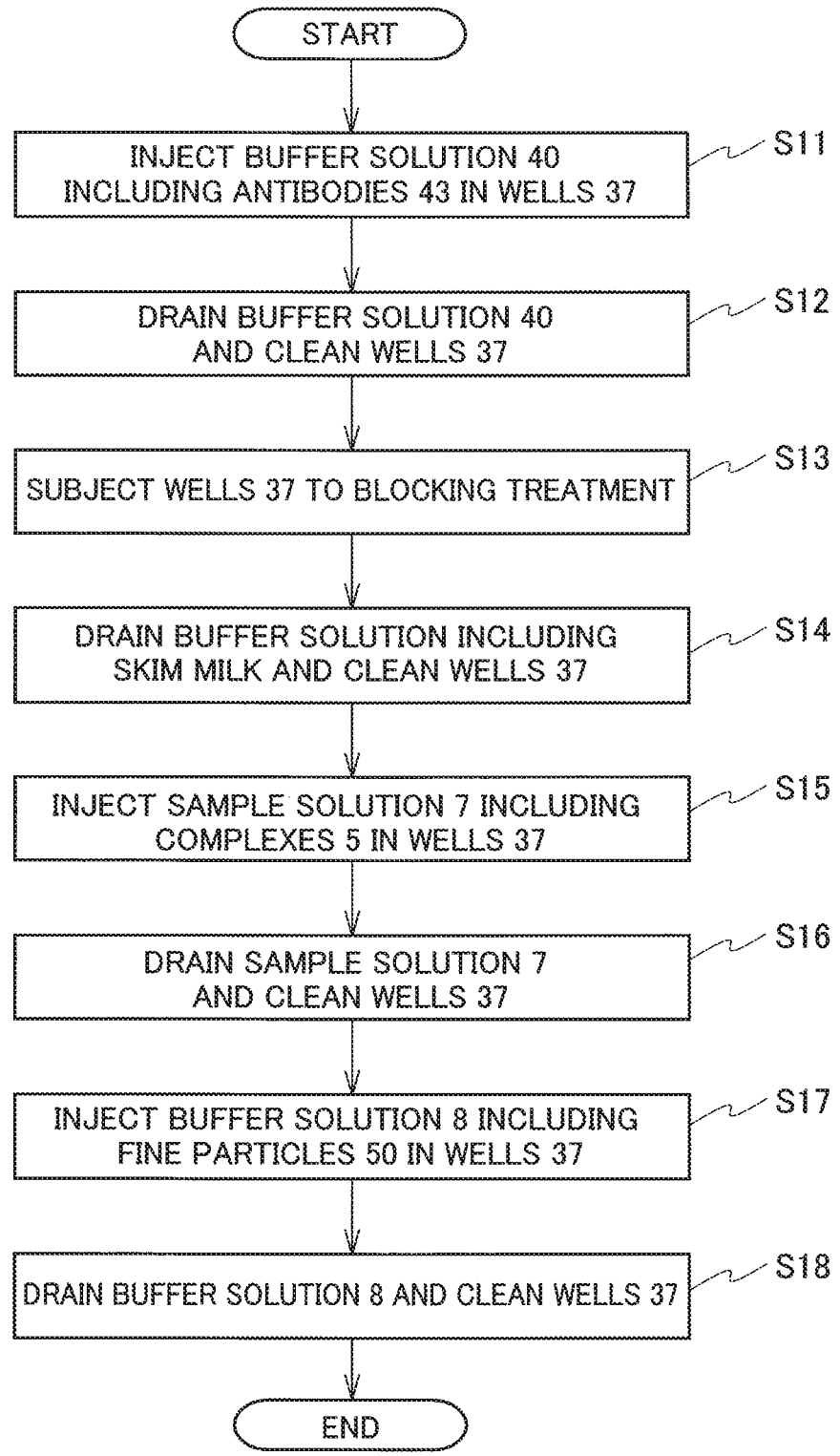
FIG. 9 is a flowchart for describing a method of capturing the exosomes.

FIG. 9 is a flow chart for describing the method of capturing the exosomes 10.

Figure 10A:
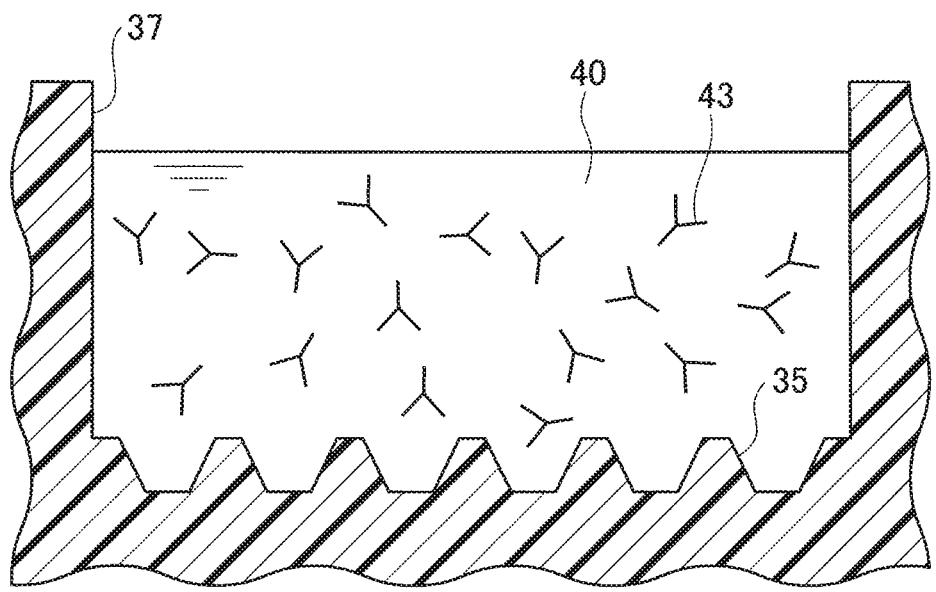
FIG. 10A is a schematic cross-sectional view of a buffer solution including antibodies injected in the well.
Figure 10B:
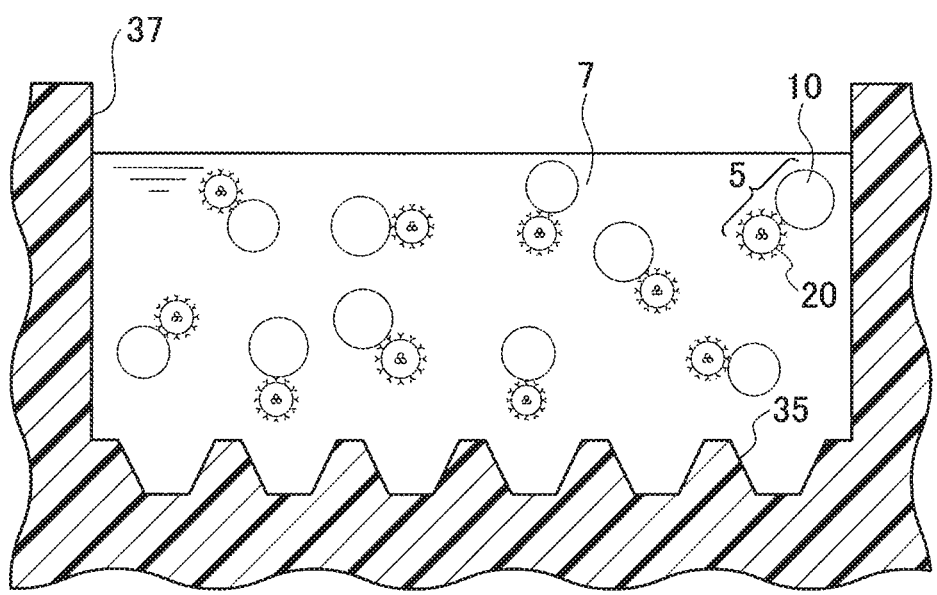
FIG. 10B is a schematic cross-sectional view of the sample solution including the complexes injected in the well.

FIG. 10A is a schematic cross-sectional view of a buffer solution 40 including antibodies 43 and injected in the well 37. FIG. 10B is a schematic cross-sectional view of the sample solution 7 including the complexes 5 and injected in the well 37. FIG. 10A and FIG. 10B each illustrate the substrate 31 and the cartridge 32 with the integrated and simplified structure.

Figure 11A:
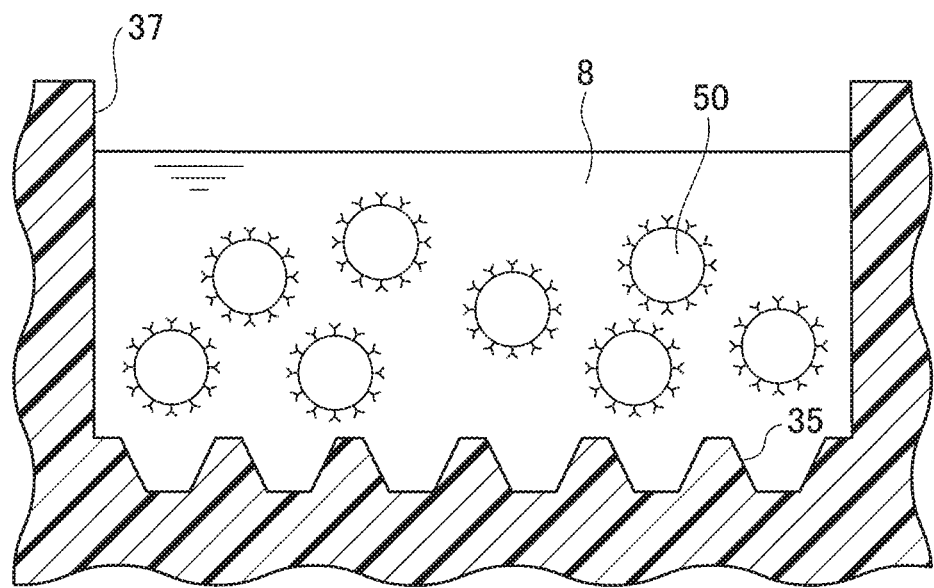
FIG. 11A is a schematic view of a buffer solution including nanoparticles injected in the well.
Figure 11B:
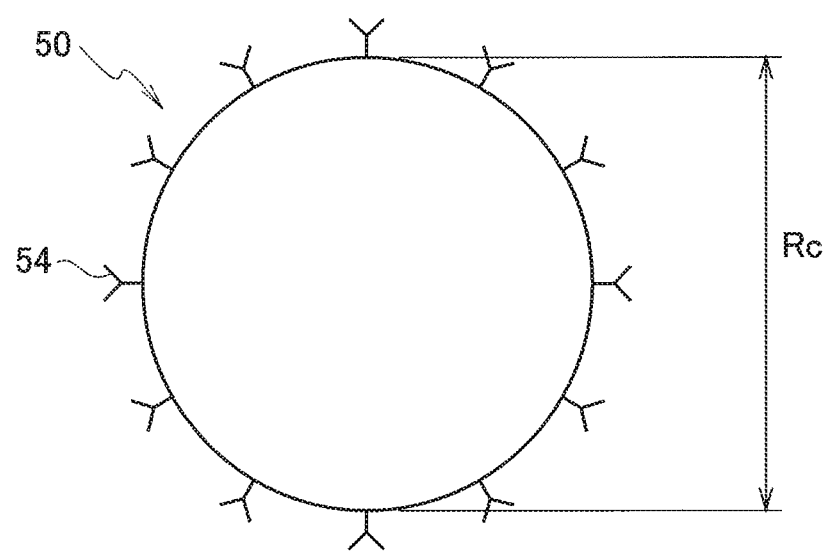
FIG. 11B is a schematic view of each fine particle.

FIG. 11A is a schematic view of a buffer solution 8 including nanoparticles 50 and injected in the well 37. FIG. 11B is a schematic view of the fine particle 50.

FIG. 12A is a schematic cross-sectional view showing a state in which the antibodies 43 are fixed to the track region 35. FIG. 12B is a schematic cross-sectional view showing a state in which a block layer 41 is formed on the track region 35.

FIG. 12A and FIG. 12B each illustrate a state in which the antibodies 43 are fixed to the substrate 31 substantially in the vertical direction. Actually, the direction in which the antibodies 43 are fixed depends on the fixation method. For example, when hydrophobic binding is used as the fixation method, the antibodies 43 are fixed to the substrate 31 in various directions.

FIG. 13A is a schematic cross-sectional view showing a state in which the complexes 5 are captured in the grooves 34 in the track region 35. FIG. 13B is a schematic cross-sectional view showing a state in which complexes 9 (second complexes) in which the magnetic nanoparticles 20 and the nanoparticles 50 bind to the exosomes 10 are captured in the grooves 34 in the track region 35.

The exosomes 10 shown in FIG. 13A and FIG. 13B correspond to the exosomes 10 shown in FIG. 2B, while being simplified and schematically shown for illustration purposes.

In step S11 shown in FIG. 9, the operator injects the buffer solution 40 including the antibodies 43 (second binding substances) which specifically bind to antigens 13 (second detection target substances) of the exosomes 10, into the wells 37 in the exosome capture unit 30, as shown in FIG. 10A.

The operator incubates the buffer solution 40 in the exosome capture unit 30 for an appropriate time at an appropriate temperature. For example, the buffer solution 40 in the exosome capture unit 30 is incubated overnight at four degrees according to a typical immunoassay. As a result, the antibodies 43 are fixed to the track region 35 on the substrate 31.

In step S12, the operator drains the buffer solution 40 from the wells 37, and cleans the wells 37 with another buffer solution. The antibodies 43 not fixed to the track region 35 are removed due to the cleaning.

Step S11 and step S12 are necessary steps when the operator fixes the antibodies 43 to the track region 35. When the exosome capture unit 30 or the substrate 31 to which the antibodies 43 are preliminarily fixed in a factory or the like is used, step S11 and step S12 can be omitted.

As shown in FIG. 12A, the antibodies 43 are fixed to the convex regions 33 and the grooves 34 provided in the track region 35 by hydrophobic binding. The method of fixing the antibodies 43 is not limited to the hydrophobic binding. The antibodies 43 may be fixed to the track region 35 by covalent binding or the like after the track region 35 is subjected to appropriate chemical treatment. The antibodies 43 may be fixed to the track region 35 according to a method used in a typical immunoassay.

In step S13, the operator subjects the inside of the wells 37 to blocking treatment in order to prevent non-specific binding of the antigens to regions other than the antigen-identifying portions of the antibodies 43. In particular, the operator injects skim milk diluted with a buffer solution into the wells 37, and subjects the exosome capture unit 30 to shaking for an appropriate time, as in the case of step S11.

The skim milk contains proteins not adhering to the exosomes 10 and is therefore preferably used for the blocking treatment. The substance used for the blocking treatment is any substance which can achieve the effects similar to the skim milk.

In step S14, the operator drains the buffer solution containing the skim milk from the wells 37, and cleans the wells 37 with another buffer solution. The buffer solution used for cleaning may contain or does not necessarily contain skim milk. The step of cleaning may be omitted.

As shown in FIG. 12B, the block layer 41 is formed on the track region 35.

In step S15, the operator injects the sample solution 7 including the complexes 5 in the wells 37, as shown in FIG. 10B, and incubates the sample solution 7 in the exosome capture unit 30 for an appropriate time at an appropriate temperature, as in the case of step S11. The exosome capture unit 30 may be subjected to shaking during the incubation. In step S15, the exosome capture unit 30 is subjected to shaking for about two hours at 37 degrees, for example.

As a result, the antigens 13 of the exosomes 10 are specifically bound to the antibodies 43 fixed to the track region 35 due to the antigen-antibody reaction. As shown in FIG. 13A, the complexes 5 are captured in the grooves 34 in the track region 35. Depending on the sample solution, the exosomes not including the antigens 13 may be present. The exosomes not including the antigens 13 are dispersed in the sample solution 7 as the complexes 5 without being bound to the antibodies 43 on the track region 35.

In step S16, the operator drains the sample solution 7 from the wells 37, and cleans the wells 37 with a buffer solution. The complexes 5 dispersed in the sample solution 7 and the complexes 5 adhering to the track region 35 by non-specific binding, which is not the antigen-antibody reaction, are removed due to the cleaning. Namely, the exosomes not including the antigens 13 dispersed in the sample solution 7 are removed through the cleaning by the buffer solution. The magnetic nanoparticles 20 included in the sample solution 7 are also removed due to this cleaning.

In step S17, the operator injects the buffer solution 8 (a second buffer solution) including the nanoparticles 50 (second nanoparticles) into the wells 37, as shown in FIG. 11A, and subjects the exosome capture unit 30 to shaking for an appropriate time, as in the case of step S11.

The fine particle 50 is made of synthetic resin such as polystyrene or glycidyl methacrylate formed into a substantially spherical shape as shown in FIG. 11B. Antibodies (third binding substances) which specifically bind to antigens 14 (third detection target substances) of the exosome 10 are fixed to the surface of the fine particle 50. A particle diameter Rc of the fine particle 50 will be described below.

The antigens 14 of the exosomes 10 are thus specifically bound to the antibodies 54 of the nanoparticles 50 by the antigen-antibody reaction. As shown in FIG. 13B, the complexes 9 in which the magnetic nanoparticles 20 and the nanoparticles 50 bind to the exosomes 10 are captured in the grooves 34 in the track region 35. The exosomes not including the antigens 14 are captured in the grooves 34 in the track region 35 without being bound to the antibodies 54 of the nanoparticles 50.

Accordingly, the complexes 9 in which the exosomes 10 expressing all of the three detection target substances (proteins) 12, 13, and 14 for identifying the exosomes 10 are bound and the complexes 5 in which the exosomes 10 expressing the two detection target substances (proteins) 12 and 13 are bound, are captured in the grooves 34 in the track region 35.

The nanoparticles 50 may enclose the magnetic substances 21, as in the case of the magnetic nanoparticles 20.

The nanoparticles 50 enclosing the magnetic substances 21 can rapidly be transferred toward the track region 35 such that a magnet is placed on the rear surface of the exosome capture unit 30 in step S17. Accordingly, a time reduction in step S17 can be achieved.

In step S18, the operator drains the buffer solution 8 from the wells 37, and cleans the wells 37 with another buffer solution. The nanoparticles 50 dispersed in the buffer solution 8 are removed due to the cleaning.

The track region 35 on which the complexes 9 and the complexes 5 are captured, more particularly, the grooves 34 is irradiated with laser light from an optical pickup externally installed, for example. The reflection light from the track region 35 is analyzed, so as to detect only the complexes 9 in which the nanoparticles 50 are bound. Accordingly, only the exosomes 10 expressing all of the three detection target substances 12, 13, and 14 for identifying the exosomes 10 can be detected.

In particular, the optical pickup includes an objective lens for condensing the laser light on the track region 35. The substrate 31 is rotated in a manner similar to a typical optical disc, and the optical pickup is moved in the radial direction of the substrate 31, so as to cause the laser light condensed by the objective lens to scan tracks (particularly the grooves 34).

The nanoparticles 50 in the complexes 9 captured in the grooves 34 can be detected according to detection signals obtained by the reflection light from the track region 35. Namely, signals from the complexes 9 in which the nanoparticles 50 are bound are only sorted from the detection signals obtained by the reflection light from the track region 35, so that the exosomes 10 included in the complexes 9 can only be detected.

Since only the complexes 9 can be detected through the detection of the nanoparticles 50, the exosomes 10 in the complexes 9 can indirectly be detected accordingly. In addition, the number of the nanoparticles 50 is counted, so that the number of the exosomes 10 can be counted indirectly.

The particle diameter of the magnetic nanoparticles 20 is set to a predetermined range so as to have magnetization sufficient for the magnetic separation and regulate a change caused to the detection signals at a sufficiently small level. The particle diameter of the magnetic nanoparticles 20 is described in detail below. A change of the detection signals thus does not appear in the complexes 5 but appears only in the complexes 9. Accordingly, the complexes 9 can only be detected without complicated signal processing.

Depending on the sample solution, the exosomes not expressing the detection target substances 12, the exosomes not expressing the detection target substances 13, or the exosomes not expressing the detection target substances 14 may be present.

In accordance with the method of capturing the exosomes according to one or more embodiments, the exosomes 10 not expressing the detection target substances 12, among the three detection target substances 12, 13, and 14, are removed in step S5. For example, when only the exosomes not expressing the detection target substances 12 are included in the sample solution, all the exosomes are removed in step S5, and therefore, the sample solution can be determined to include only the exosomes not expressing the detection target substances 12.

In accordance with the method of capturing the exosomes according to one or more embodiments, the exosomes 10 not expressing the detection target substances 13 are removed in step S16. The exosomes not expressing the detection target substances 14 are not bound to the nanoparticles 50 and therefore not detected. Thus, the exosomes 10 expressing the three detection target substances 12, 13, and 14 can only be detected.

The method of capturing the exosomes according to one or more embodiments can therefore identify the three kinds of proteins present on one exosome simultaneously. When the sample solution does not include the exosomes expressing all the three detection target substances, no exosome is detected, so that the sample solution can be determined not to include the exosomes expressing all the three detection target substances. Accordingly, the disease specificity can further be enhanced, and the precision or accuracy of diagnoses can further be improved.

A mutual relationship among the exosomes 10, the magnetic nanoparticles 20, the nanoparticles 50, and the track region 35 is described below with reference to FIG. 14 and FIG. 15.

Figure 14:
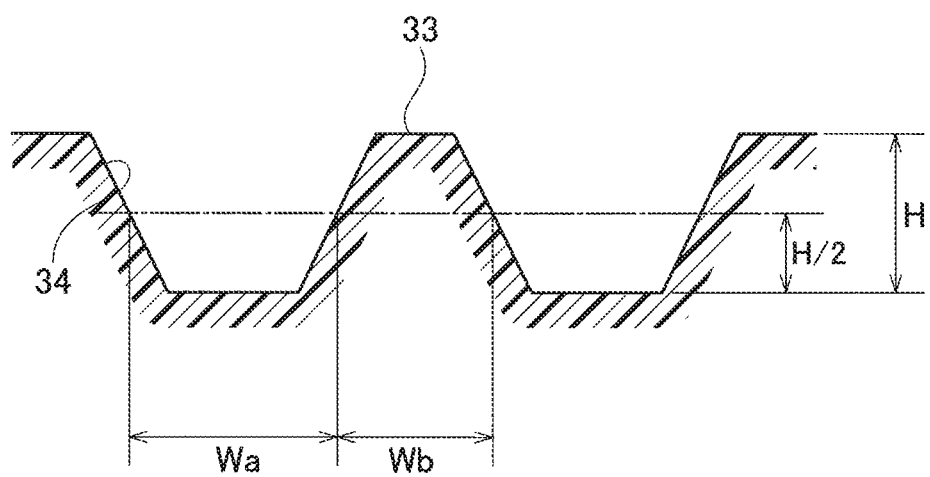
FIG. 14 is an enlarged cross-sectional view showing dimensions of convex regions and grooves in the track region.

FIG. 14 is an enlarged cross-sectional view showing the dimensions of the convex regions 33 and the grooves 34 in the track region 35. The depth of the grooves 34 (the height of the convex regions 33) is indicated by symbol H, the width of the grooves 34 is indicated by symbol Wa, and the width of the convex regions 33 is indicated by symbol Wb. The width Wa and the width Wb are each measured at a position indicated by the dash-dotted line with symbol H/2.

Figure 15A:
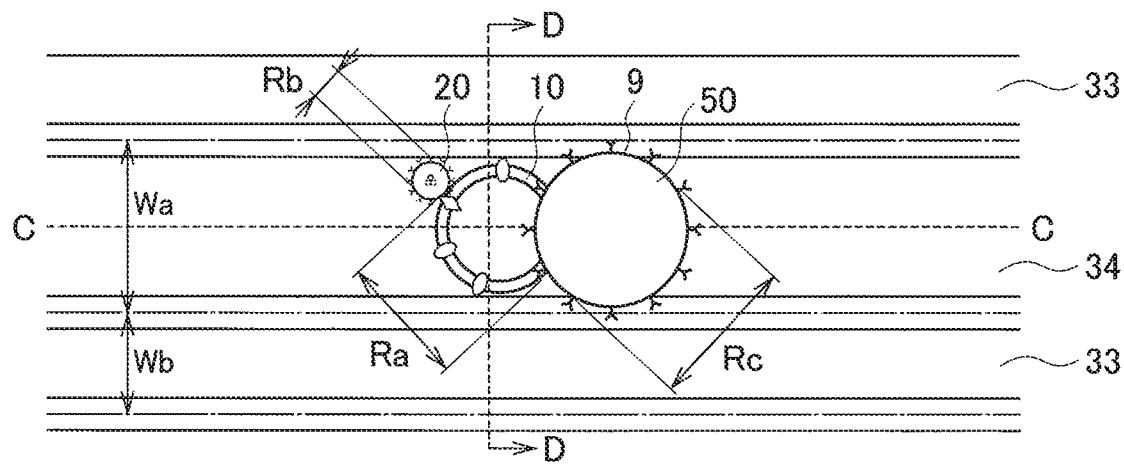
FIG. 15A is a schematic top view showing a state in which the complex is fixed to the groove in the track region.
Figure 15B:
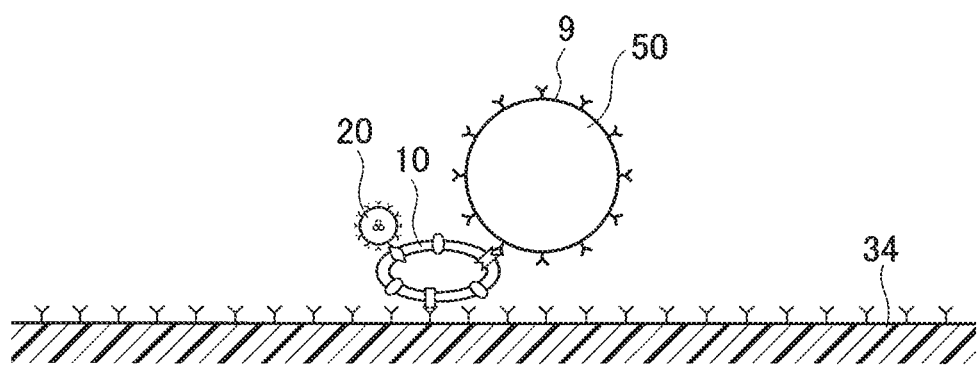
FIG. 15B is a schematic cross-sectional view taken along line C-C in FIG. 15A.
Figure 15C:
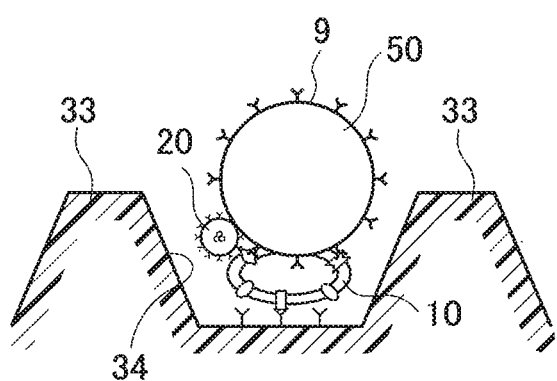
FIG. 15C is a schematic cross-sectional view taken along line D-D in FIG. 15A.

FIG. 15A is a schematic top view showing a state in which the complex 9 is fixed to the groove 34 in the track region 35. FIG. 15B is a schematic cross-sectional view taken along line C-C in FIG. 15A. FIG. 15C is a schematic cross-sectional view taken along line D-D in FIG. 15A.

As shown in FIG. 15A to FIG. 15C, the exosomes 10 are arranged in the track direction, and one exosome 10 is bound to one fine particle 50 with a high probability, so as to improve the precision or accuracy in the measurement of the exosomes 10.

For example, as shown in the following expression (1), the particle diameter Rb of the magnetic nanoparticles 20 is preferably smaller than a spot diameter $(k \times \lambda)/NA$ of the laser light condensed on the grooves 34, and the particle diameter Rc of the nanoparticles 50 is preferably greater than or equal to the spot diameter $(k \times \lambda)/NA$.

$$Rb < (k \times \lambda)/NA \leq Rc \tag{1}$$

The symbol $\lambda$ is a center wavelength of the laser light emitted from the optical pickup and condensed on the grooves 34 by the objective lens. The symbol NA is a numerical aperture of the objective lens. The symbol k is a coefficient which is 1/5, for example.

When the expression (1) is fulfilled, the optical pickup can detect the nanoparticles 50 precisely without being influenced by the magnetic nanoparticles 20. Accordingly, the precision or accuracy in the measurement of the nanoparticles 50 can be improved. In the case of $\lambda$=405 nm, NA=0.85, and k=1/5, the spot diameter $(k \times \lambda)/NA$ is 95 nm. The particle diameter Rb of the magnetic nanoparticles 20 is thus less than 95 nm, preferably about 50 nm. The particle diameter Rc of the nanoparticles 50 is 200 nm, for example.

As shown in the following expression (2), the width Wb of the grooves 33 is preferably smaller than the average particle diameter Ra of the exosomes 10.

$$Wb < Ra \tag{2}$$

When the expression (2) is fulfilled, the complexes 5 are not easily positioned on the grooves 33.

As shown in the following expression (3), the width Wa of the grooves 34 is preferably greater than the sum of the average particle diameter Ra of the exosomes 10 and the particle diameter Rb of the magnetic nanoparticles 20 and smaller than four times the average particle diameter Ra.

$$(Ra+Rb) < Wa < 4 \times Ra \tag{3}$$

When the relationship of $(Ra+Rb) < Wa$ in the expression (3) is fulfilled, the complexes 5 can be captured in the grooves 34.

As shown in FIG. 13A, the exosomes 10 captured in the grooves 34 are generally deformed from the spherical shape in a direction in which the contact area is increased. When the nanoparticles 50 enclosing the magnetic substances 21, similar to the magnetic nanoparticles 20, are used, the deformation of the exosomes 10 is promoted due to the magnetic force of the magnet placed on the rear surface of the exosome capture unit 30 in step S17.

When each spherical exosome 10 is assumed to be deformed to have an ellipsoid while keeping the volume, and the diameter of the ellipsoid is changed by 50%, the diameter at a portion in contact with the grooves 34, which is the major axis of the ellipsoid of revolution, is increased by 40%. Actually, since the exosome 10 is deformed in the direction in which the area at the contact portion is increased more than the ellipsoid of revolution, the diameter at the contact portion is increased by 50% or more of the diameter of the original spherical shape, or increased by 100% or more depending on the circumstances.

Thus, it is preferable to fulfill the relationship of $Wa < 4 \times Ra$ in the expression (3).

As shown in the following expression (4), the width Wb of the convex regions 33 is preferably smaller than the particle diameter Rc of the nanoparticles 50. The width Wa of the grooves 34 is preferably greater than the particle diameter Rc and smaller than two times the particle diameter Rc.

$$Wb < Rc < Wa < 2 \times Rc \tag{4}$$

When the relationship of $Wb < Rc$ in the expression (4) is fulfilled, the nanoparticles 50 are not easily positioned on the convex regions 33. When the relationship of $Rc < Wa$ in the expression (4) is fulfilled, the nanoparticles 50 can enter the grooves 34. When the relationship of $Wa < 2 \times Rc$ in the expression (4) is fulfilled, two nanoparticles 50 are not easily laid simultaneously in the groove 34 in the width direction, so that the numerical relationship between the exosomes 10 and the nanoparticles 50 bound together can approximate to one to one.

As shown in the following expression (5), the particle diameter Rc of the nanoparticles 50 is preferably greater than the average particle diameter Ra of the exosomes 10.

$$Ra < Rc \tag{5}$$

When the expression (5) is fulfilled, a plurality of nanoparticles 50 do not easily bind to one exosome 10 fixed to the groove 34, so that the numerical relationship between the exosomes 10 and the nanoparticles 50 bound together can approximate to one to one. In addition, when the expression (5) is fulfilled, the probability that the exosomes 10 and the nanoparticles 50 meet to react with each other increases, so as to improve the yield of the reaction between the exosomes 10 and the nanoparticles 50 accordingly.

As shown in the following expression (6), the depth H of the grooves 34 is preferably greater than 1/8 of the sum of the average particle diameter Ra of the exosomes 10 and the particle diameter Rc of the nanoparticles 50.

$$(Ra+Rc)/8 < H \tag{6}$$

When the expression (6) is fulfilled, the exosomes 10 are easily captured in the grooves 34, and the adhesion of the fine particle 50 to the convex regions 33 by non-specific binding hardly occurs, so that the nanoparticles 50 can easily bind to the exosomes 10 captured in the grooves 34.

The depth H of the grooves 34 more preferably fulfills the following expression (7).

$$(Ra+Rc)/6<H \tag{7}$$

It is preferable to fulfill all of the expression (1) to the expression (6) (or the expression (7)), but not all the expressions are necessarily fulfilled.

It should be understood that the present invention is not intended to be limited to one or more embodiments described above, and various modifications will be apparent to those skilled in the art without departing from the scope of the present invention.

The present invention is applicable to the case of capturing exosomes for detecting diseases and the like.

What is claimed is:

1. A method of capturing exosomes comprising the steps of:
    mixing a first sample solution including exosomes expressing first detection target substances, second detection target substances, and third detection target substances with a first buffer solution including first nanoparticles fixing first binding substances which bind to the first detection target substances, so as to bind the first detection target substances and the first binding substances together to form first complexes of the exosomes and the first nanoparticles;
    isolating the first complexes from a mixed solution of the first sample solution and the first buffer solution;
    binding the second detection target substances of the first complexes and second binding substances which bind to the second detection target substances together, so as to capture the first complexes on a substrate, the second binding substances being fixed onto the substrate; and
    reacting a second buffer solution including second nanoparticles fixing third binding substances which bind to the third detection target substances with the first complexes captured on the substrate, and binding the third detection target substances and the third binding substances together, so as to bind the second nanoparticles to the exosomes of the first complexes which are captured on the substrate.

2. The method of capturing the exosome according to claim 1, wherein the second nanoparticles in the second complexes captured on the substrate are detected so as to indirectly detect the exosomes in the second complexes.

3. The method of capturing the exosome according to claim 1, wherein a particle diameter of the first nanoparticles is smaller than a particle diameter of the second nanoparticles.

4. The method of capturing the exosomes according to claim 1, wherein the substrate includes a track region provided with convex regions and grooves arranged alternately, and the first complexes and the second complexes are captured in the grooves.

* * * * *